United States Patent
Baisden

[19]

[11] Patent Number: 5,924,138
[45] Date of Patent: Jul. 20, 1999

[54] APPARATUS AND METHODS FOR AURAL PROTECTION

[76] Inventor: Joseph T. Baisden, Rte. 1, Box 1200-3, Morriston, Fla. 32668

[21] Appl. No.: 08/831,447

[22] Filed: Apr. 1, 1997

[51] Int. Cl.⁶ .................................................. A61F 11/14
[52] U.S. Cl. ............................... 2/209; 351/123; 351/158
[58] Field of Search ................................ 2/209, 423, 10, 2/13; 351/123, 158; 381/388

[56] References Cited

U.S. PATENT DOCUMENTS

| | | |
|---|---|---|
| 4,174,155 | 11/1979 | Herman . |
| 4,670,911 | 6/1987 | Dunford ........................................ 2/209 |
| 5,092,667 | 3/1992 | Bagley ................................ 351/123 X |
| 5,201,856 | 4/1993 | Edwards . |
| 5,278,999 | 1/1994 | Brown et al. ........................ 351/158 X |

FOREIGN PATENT DOCUMENTS

| | | |
|---|---|---|
| 2706382 | 8/1977 | Germany ..................................... 2/209 |
| 2708063 | 8/1977 | Germany ..................................... 2/209 |

*Primary Examiner*—Peter Nerbun
*Attorney, Agent, or Firm*—Saliwanchik, Lloyd & Saliwanchik

[57] ABSTRACT

The present invention pertains to a hearing protective earmuff apparatus for use by an individual wearing eyeglasses while effecting a complete seal of the earmuff pad against the individual's head. In one embodiment, the earmuff comprises an outer housing assembly, a resilient inner pad that can seal against the wearer's head, and a middle assembly positioned between the outer housing assembly and the inner pad. The middle assembly includes an eyeglass stem receptor channel that opens at the front of the middle assembly. The receptor channel is adapted to receive and removably engage an eyeglass ear stein inserted into the stem receptor. In another embodiment, the earmuff apparatus of the invention comprises a pair of auditory protective earmuffs mounted on a connecting band.

11 Claims, 4 Drawing Sheets

APPARATUS AND METHODS FOR AURAL PROTECTION

BACKGROUND OF THE INVENTION

It is a common problem in today's industrial world for individuals to be exposed to prolonged and/or high decibel levels of sound. For example, persons in work environments such as commercial aviation, factories, steel mills, power plants and the like, may be exposed to noise and sound levels that can result in temporary and/or permanent damage to their hearing. It is known that damage to a person's hearing can occur before the exposure to a sound becomes physically painful to the person.

Because of the possibility of hearing damage and loss in persons working in certain environments or participating in certain activities, many private, state, and federal safety regulations require workers to wear hearing protection, such as sound absorbing earplugs or earmuffs. In many environments, earplugs do not block a sufficient amount of noise or are not accepted hearing protection; thus, earmuffs are often tile only accepted or useful means for protecting a person's hearing.

Earmuffs provide aural protection by fitting and sealing tightly to a person's head around their outer ears. This tight seal to the head, around the outer ear, along with other materials used in the construction of the earmuff, prevents air and sound from penetrating the protective barrier to the ear provided by the earmuff. Various types of conventional sound protective earmuffs are known in the art. For example, U.S. Pat. No. 4,674,134 discloses an earmuff having a sealing ring composed of liquid and foam that fits around the wearer's outer ear.

Although earmuffs can provide protection from sound and noise, it is not uncommon that individuals that are required or that choose to wear sound absorbing earmuffs must also wear eyeglasses, such as prescription eyeglasses for purposes of correcting vision, or safety glasses for protection of eyesight. Unfortunately, in order to wear eyeglasses in conjunction with earmuffs it is necessary to insert the eyeglass ear stem between the earmuff pad and the head of a user, resulting in the earmuff pad being pressed against the eyeglass frame stem, thereby disrupting the seal of the earmuff around the person's ear and allowing air and sound to enter. To be effective as a hearing protection device, the tight, flush seal of an earmuff against the wearer's head must not be disrupted.

U.S. Pat. No. 4,174,155 discloses a sound absorbing article that attaches to the ear stem of eyeglasses. The article is designed to be used in conjunction with earmuffs in a manner such that gaps that might be formed between the earmuff and the stem of the eyeglasses are filled in by the article. However, it appears unlikely that the article disclosed in the '155 patent would completely eliminate gaps near where the earmuff contacted the sound absorbing article. In addition, it appears that the eyeglass ear stein with the sound absorbing article attached would be difficult to insert between the earmuff pad and the user's head without first lifting the earmuff pad away from the head and thereby, at least temporarily, breaking the seal between the earmuff pad and the user's head.

Accordingly, there remains a need in the art for a device that will protect a person from excessive sound and noise, yet allow the person to comfortably wear eyeglasses or safety glasses without impairing the hearing protection provided by the device. The present invention comprises a simple, effective earmuff apparatus to provide hearing protection for persons that also wear eyeglasses.

BRIEF SUMMARY OF THE INVENTION

The subject invention concerns a novel protective earmuff apparatus for use by individuals wearing eyeglasses. The subject apparatus comprises a means for receiving and securing the ear stems of eyeglasses within an earmuff assembly, thereby avoiding breaking the seal of the earmuff against the individual's head. In a specific embodiment, the earmuff apparatus comprises an outer housing assembly, a resilient annular inner pad that can cover the outer ear and fit snugly against the wearer's head, and a middle assembly positioned between the outer housing assembly and the inner pad. The middle assembly can include an eyeglass stein receptor channel having a stein guide that forms the roof of the receptor channel, and an aperture, forming the mouth of the receptor channel, at the front of the middle assembly. The receptor channel can receive and tightly engage an eyeglass ear stem inserted therein by, for example, a means for biasing the eyeglass ear stem against the ear stem guide of the receptor channel. In a preferred embodiment, the earmuff apparatus of the subject invention comprises a pair of protective earmuffs of the present invention mounted on a connecting band for imparting force to hold the earmuffs securely against the person's head.

The subject invention also concerns a method for providing hearing protection to a person wearing eyeglasses.

DETAILED DISCLOSURE OF THE INVENTION

The subject invention concerns a novel earmuff apparatus for use by persons wearing eyeglasses, such as prescription eyeglasses or safety glasses. The earmuff apparatus comprises novel means for receiving and securing the ear stems of eyeglass frames within the earmuff. Advantageously, the present invention securely and comfortably holds the eyeglasses in place on the wearer's face yet avoids the problem of an eyeglass ear stem breaking the seal of an earmuff against the wearer's head and impairing the protective function of the earmuff. As used herein, the term "eyeglasses" refers to any type of optical device secured in a frame having ear stems that when worn covers the wearer's eyes, and includes, for example, corrective eyeglasses, protective safety glasses, and sunglasses.

Figure 1A:
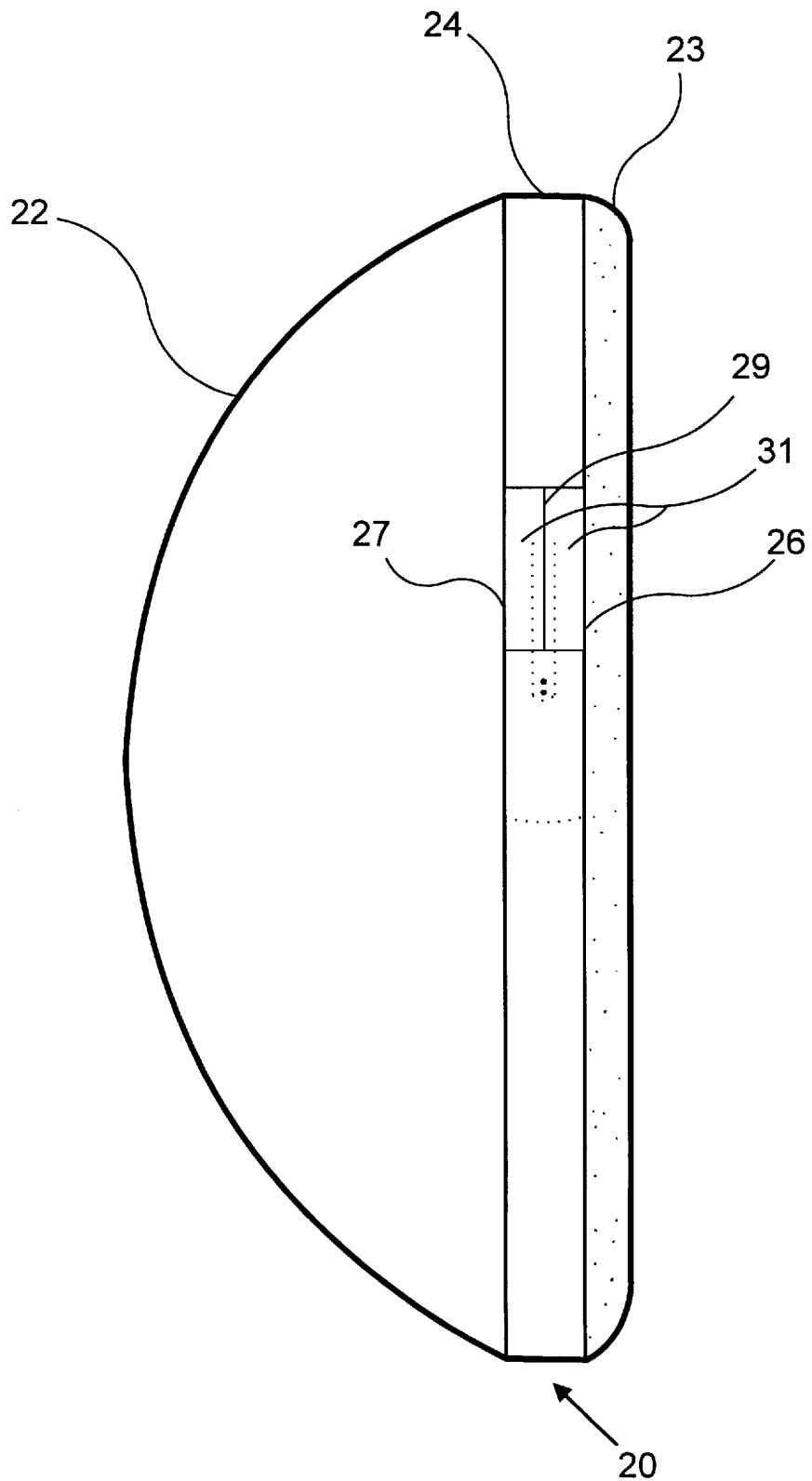
FIG. 1A shows a schematic, frontal view of an earmuff in accordance with the subject invention.
Figure 1B:
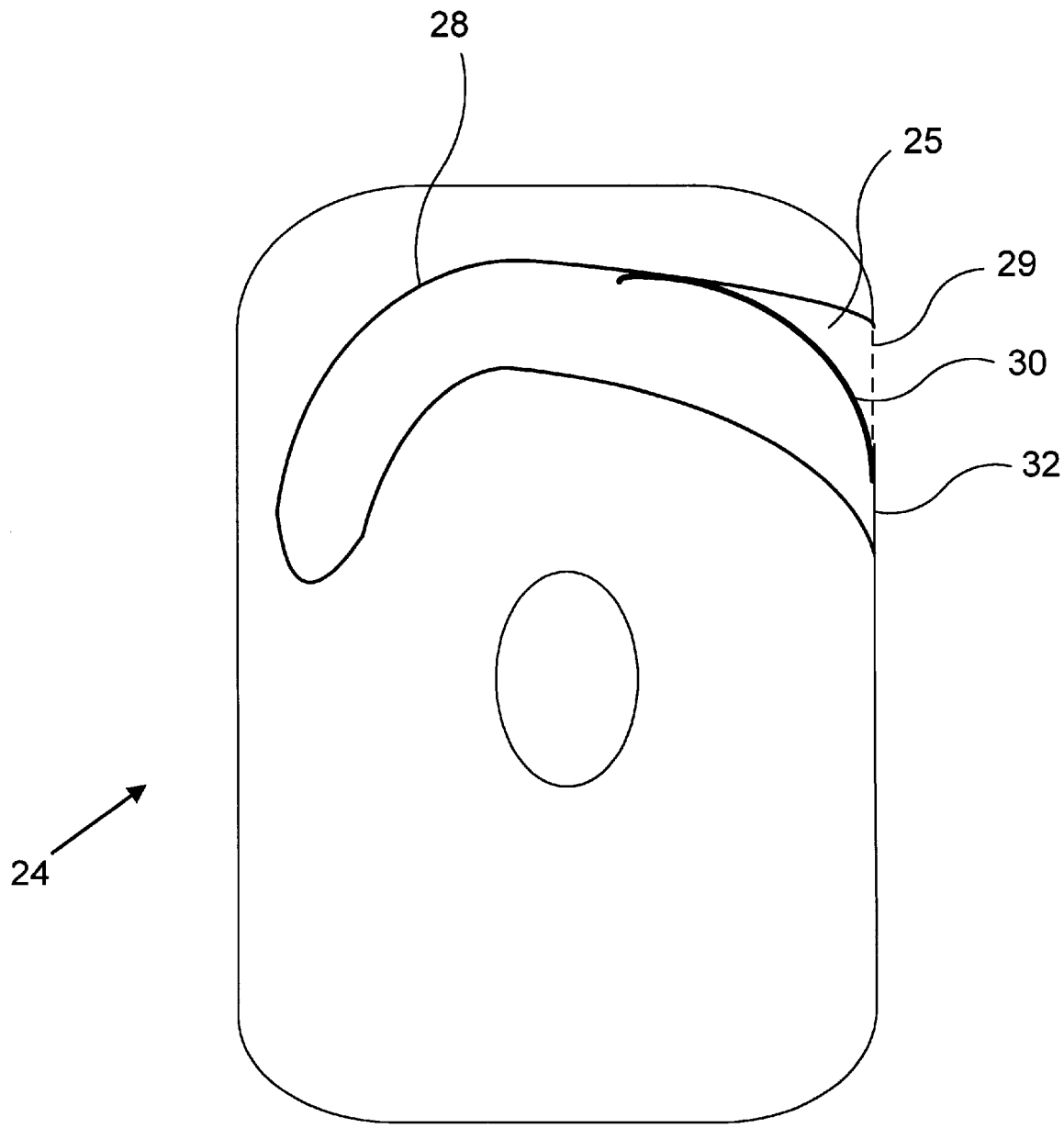
FIG. 1B shows a schematic, side view of a middle assembly in accordance with the subject invention.

Referring to FIGS. 1A and 1B, an earmuff 20 according to the subject invention can comprise an outer housing assembly 22, a resilient inner pad assembly 23 which can fit snugly against the wearer's head, and a middle assembly 24 positioned between the outer housing assembly 22 and inner pad assembly 23. The outer, middle and inner assemblies can be secured together using standard means known in the art, such as pins, screws, rivets, and/or adhesives. Resilient inner pad assembly 23 can be substantially annular in design to fit snugly against a person's head and around their outer ear. Inner pad assembly 23 is typically constructed of foam, liquid, gel, or some other pliable material and covered in cloth, leather, plastic or other suitable materials.

Referring to FIG. 1B, middle assembly 24 can include an eyeglass ear stem receiving means for engagably receiving an eyeglass ear stem. In a preferred embodiment, a stem receiving means comprises eyeglass ear stem receptor channel 25. Eyeglass ear stem receptor channel 25 can be of any cross-sectional configuration, for example, cylindrical, tubular, rectangular, or any other shape, which allows reception of and means for securely engaging an ear stem. Channel 25 can have one, two, three or more sides, or can be formed of curved surfaces. As illustrated in FIG. 1A, eyeglass ear stem receptor channel 25 can, for example, be formed by adjacent first 26 and second 27 side walls of the middle assembly and bounded at the top and/or bottom by an eyeglass ear stem guide 28. First 26 and second 27 side walls can extend from the top to the bottom of receptor channel 25. Alternatively, first 26 and/or second 27 side walls can extend further, for example from the top to the bottom of the middle assembly 24. If first 26 and/or second 27 side walls extend the length of the middle assembly, apertures can be located on side walls 26, 27 to allow sound waves to penetrate side walls 26, 27. Preferably, stem guide 28 has substantially the same contour as an ear stem of eyeglasses used in accordance with the present invention. The receptor channel 25 includes a receptor channel aperture 29 for receiving eyeglass ear stems, wherein eyeglass ear stems can be inserted through aperture 29 and into receptor channel 25. Once the eyeglass ear stems are inserted into receptor channel 25, the subject invention provides a means for securing the ear stems within the receptor channel in order to hold the eyeglasses securely in place with respect to a person wearing the eyeglasses. A securing means can, for example, comprise a means for applying sufficient force to the inserted ear stems to hold the ear stems securely within receptor channel 25.

In one embodiment, when an eyeglass ear stem is inserted through aperture 29 and into receptor channel 25 of the subject earmuff, the stem can be securely engaged by a biasing means for urging the ear stem against an ear stem guide 28 that forms the top and/or bottom of receptor channel 25 and/or against either of first 26 or second 27 side walls. In a preferred embodiment, the biasing means comprises a flexible, resilient member 30 disposed within the middle assembly 24 of the earmuff apparatus 20 and can be attached, for example, to outer casing 32 of middle assembly 24. Resilient member 30 releasably engages an eyeglass stem inserted in receptor channel 25 by applying an effective amount of pressure on the eyeglass stem to hold the eyeglass stem against stem guide 28 and/or first 26 or second 27 side walls and, therefore, securely inside eyeglass stem receptor channel 25. Other biasing means known in the art are contemplated within the scope of the present invention.

In a preferred embodiment, receptor channel aperture 29 includes a closure means 31 for sealing aperture 29 around an inserted eyeglass ear stem in order to minimize sound waves entering aperture 29 when an ear stem is inserted into aperture 29. Closure means 31 can also seal aperture 29 when no eyeglass ear stem is inserted into receptor channel 25, to minimize sound waves penetrating into receptor channel 25 when no ear stem is inserted. More preferably, the closure means 31 comprises an acoustically opaque material, such as soft foam or rubber pieces, attached to first 26 and/or second 27 side walls of receptor channel 25, or to outer casing 32. In a specific embodiment, closure means 31 can also function to secure the inserted ear stem in place, eliminating the need for a separate securing means.

In a preferred embodiment, receptor channel 25 of middle assembly 24 is aurally isolated so that any sounds entering through aperture 29 and into receptor channel 25 are prevented from reaching, or attenuated prior to entering, a user's ear. This isolation can be accomplished, for example, by the placement of sound absorbing material around middle assembly 24 in a manner that acoustically isolates middle assembly 24 from the ear of a user.

In an alternative embodiment of the present invention, ear stem receptor channel 25 can be incorporated into inner pad assembly 23. Advantageously, this location for ear stem receptor channel 25 can allow the ear stem to rest close to a user's head and can even allow the ear stem to rest between the top of a user's ear and the users head; thus, the ear stem rests in substantially the same location, relative to the user's head and ear, as when eyeglasses are worn by the user in the absence of earmuffs. With respect to this embodiment, it is preferred to enclose ear stem receptor channel 25 within the foam, liquid, gel, or other pliable material of which inner pad assembly 23 comprises. In an additional alternative embodiment, ear stem receptor channel 25 can be incorporated into outer housing assembly 22.

In another alternative embodiment, an ear stem receptor channel 25 can be inserted into existing earmuffs, thus avoiding the expense associated with purchasing new earmuffs. It is preferred, when retrofitting existing earmuffs in this way, that ear stem receptor channel 25 be aurally isolated such that sounds entering aperture 29 are prevented from reaching, or attenuated before reaching a user's ear. In a specific embodiment, middle assembly 24 can be inserted between an outer housing assembly 22 of an existing earmuff and a resilient inner pad 23 of an existing earmuff. In this embodiment, middle assembly 24 can comprise an ear stem receptor channel 25. In an alternative embodiment, existing earmuffs can have a hole drilled in an appropriate location and an ear stem receptor 25 according to the present invention inserted into the hole and securely mounted within the existing earmuff assembly. Accordingly, after secure mounting of ear stem receptor channel 25, an ear stem can be inserted into the ear stem receptor channel 25 to securely hold a user's eyeglasses in position. When utilizing the subject invention to retrofit an existing earmuff with an ear stem receptor channel 25, other modifications to the existing earmuff may be necessary and/or preferred. Such modifications would be apparent and could be readily performed by an ordinarily skilled artisan.

Figure 2:
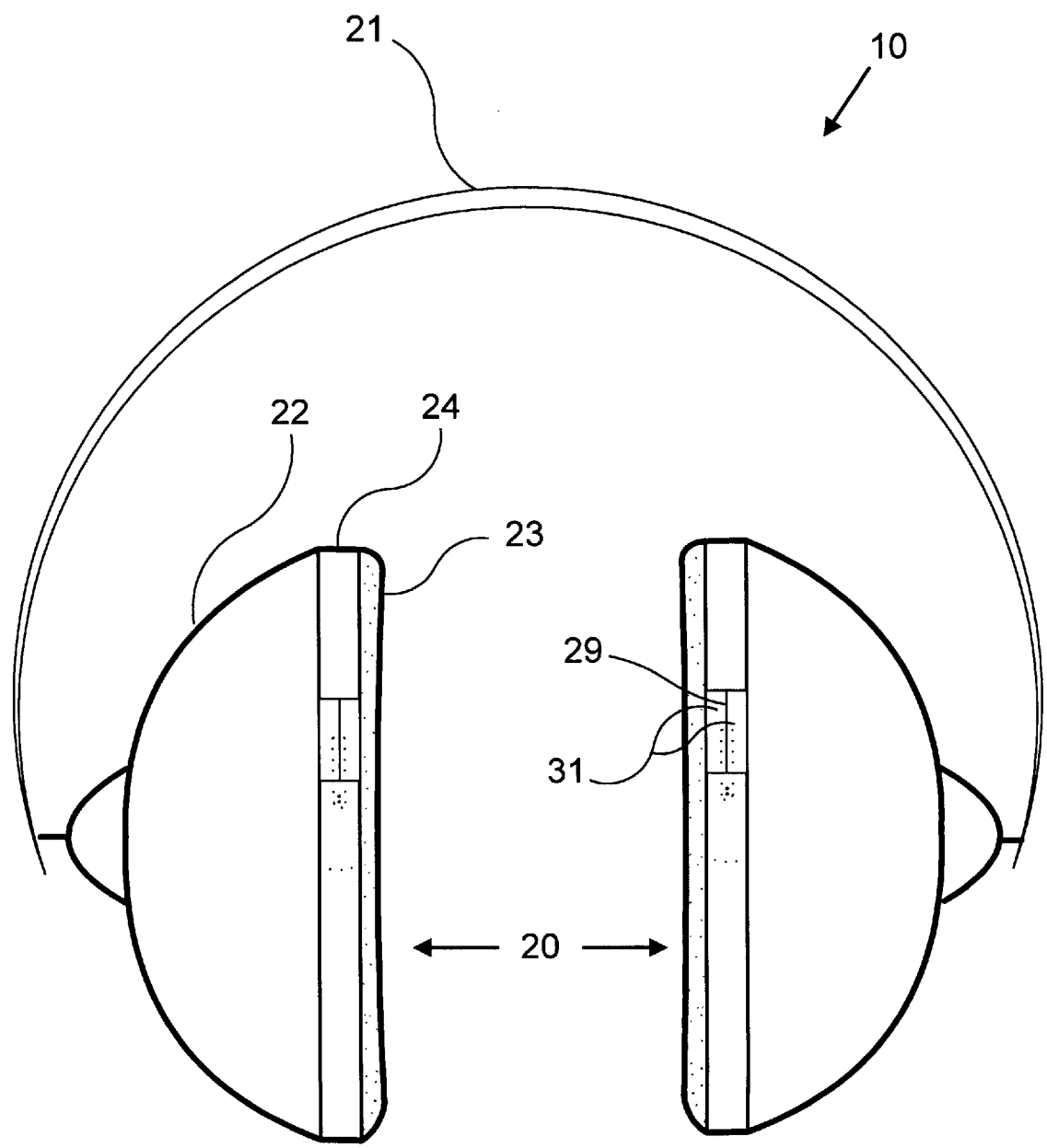
FIG. 2 shows a schematic, frontal view of a pair of earmuffs mounted on a connecting band in accordance with the subject invention.
Figure 3:
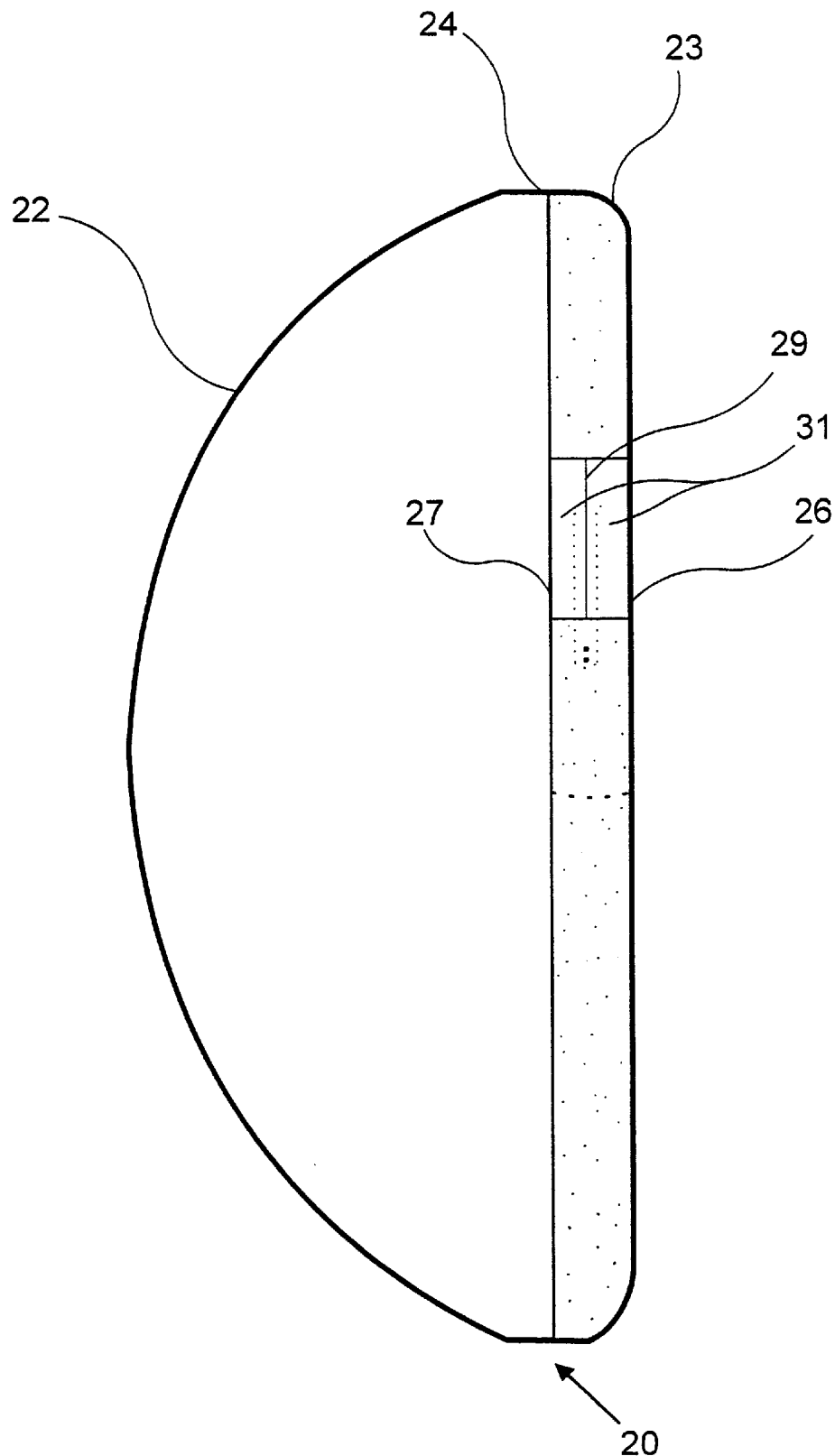
FIG. 3 shows a schematic frontal view of an earmuff with an car stem receptor channel incorporated into the inner pad assemnbly, in accordance with the subject invention.

As is shown in FIG. 2, in a preferred embodiment of the subject invention, an earmuff apparatus 10 of the invention comprises a pair of hearing protective earmuffs 20 mounted on each end of a connecting means, for example, a band 21 capable of imparting opposite inward force to hold earmuffs 20 against the wearer's head. In an alternative embodiment, an earmuff 20 can be mounted directly on a fastening member of a headwear apparatus such as a protective helmet or a hard hat. The subject invention can be used with or without a protective helmet or hard hat without compromising the effectiveness of either protective device.

To use the subject apparatus illustrated in FIG. 2, a user places an earmuff of the present invention over the user's ear such that the inner pad assembly 23 covers the ear and creates a tight, flush contact with the user's head around the outer ear. The user then inserts an eyeglass ear stem through aperture 29 and into receptor channel 25 until a proper fit is achieved. The user then wears the earmuffs as normal with the eyeglasses held in place by the earmuffs.

The subject invention also concerns a method for providing hearing protection to a person wearing eyeglasses. The method comprises placing the hearing protective earmuff apparatus of the subject invention over the ear of a user and inserting eyeglass ear stems into the earmuff apparatus of the subject invention. The method of the present invention provides for securing of the wearer's eyeglasses on their face while maintaining flush contact between the earmuff and the individual's head.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. An earmuff apparatus for providing hearing protection to an individual, said apparatus comprising a pair of protective earmuffs mounted on opposite ends of a connecting band, each said earmuff comprising an outer housing assembly, a resilient annular inner pad, and a middle assembly positioned between said outer housing assembly and said inner pad, said middle assembly comprising a receptor channel having an aperture at one end and adapted for engagably receiving an eyeglass frame ear stem, a stem guide adjacent said aperture, and biasing means for urging an eyeglass frame ear stem against said ear stem guide upon insertion of an ear stein through said aperture and into said receptor channel.

2. The earmuff apparatus, according to claim 1, wherein said means for biasing an ear stem comprises a flexible, resilient member disposed within said middle assembly.

3. The earmuff apparatus, according to claim 1, wherein said receptor channel aperture comprises closure means for sealing said aperture around an eyeglass ear stem.

4. The earmuff apparatus, according to claim 3, wherein said closure means for sealing said aperture around an eyeglass ear stem comprises a material selected from the group consisting of foam and rubber, wherein said material is attached to said receptor channel.

5. The earmuff apparatus, according to claim 3, wherein said closure means for sealing said aperture around an eyeglass ear stem comprises a material selected from the group consisting of foam and rubber, wherein said material is attached to said aperture.

6. An earmuff apparatus, according to claim 1, wherein said stem guide has substantially the same contour as an eyeglass frame ear stem.

7. An earmuff for providing hearing protection to a user, said earmuff comprising:

an outer housing assembly;

a resilient inner pad;

an aperture on said earmuff;

a means adjacent said aperture for receiving an eyeglass ear stem, wherein said receiving means comprises an eyeglass ear stem receptor channel; and a means for securing said ear stem within said receptor channel, wherein a user can insert an eyeglass ear stem through said aperture and into said receiving means while wearing said earmuff without breaking a seal between said earmnuff and the user, wherein said means for receiving an eyeglass ear stem provides structure below, sideways, and above the aperture, wherein once inserted the ear stem is held securely in place, and wherein said securing means comprises a means for biasing said ear stem against said receptor channel.

8. The earmuff, according to claim 7, wherein said biasing means comprises a flexible, resilient member.

9. An earmuff for providing hearing protection to a user, said earmuff comprising:

an outer housing assembly;

a resilient inner pad;

an aperture on said earmuff;

a means for sealing said aperture when an eyeglass ear stem is inserted through said aperture;

a means adjacent said aperture for receiving an eyeglass ear stem, wherein said receiving means comprises an eyeglass ear stem receptor channel; and a means for securing said ear stem within said receptor channel, wherein a user can insert an eyeglass ear stem through said aperture and into said receiving means while wearing said earmuff without breaking the seal between said earmuff and the user, wherein said means for receiving an eyeglass ear stem provides structure below, sideways, and above the aperture, and wherein once inserted the ear stem is held securely in place.

10. The earmuff, according to claim 9, wherein said sealing means also seals said aperture when no ear stem is inserted through said aperture and into said receiving means.

11. The earmuff, according to claim 9, wherein said sealing means also functions as said means for securing said ear stem within said receptor channel.

* * * * *

UNITED STATES PATENT AND TRADEMARK OFFICE
CERTIFICATE OF CORRECTION

PATENT NO. : 5,924,138
DATED : July 20, 1999
INVENTOR(S) : Joseph T. Baisden

It is certified that error appears in the above-identified patent and that said Letters Patent is hereby corrected as shown below:

Abstract, line 11: "ear stein" should read --ear stem--.

Column 1, line 20: "tile only" should read --the only--.

Column 2, line 12: "eyeglass stein" should read --eyeglass stem--;

line 13: "a stein guide" should read --a stem guide--; and line 37: "an car stem" should read --an ear stem--.

Column 3, line 55: "ear stern" should read --ear stem--.

Column 5, line 25: "ear stein" should read --ear stem--.

Column 6, line 12: "earmnuff" should read --earmuff--.

Signed and Sealed this

Fourth Day of January, 2000

*Attest:*

*Attesting Officer*    *Acting Commissioner of Patents and Trademarks*